(12) United States Patent
Garcia Molina et al.

(10) Patent No.: US 11,172,865 B2
(45) Date of Patent: Nov. 16, 2021

(54) SYSTEM AND METHOD FOR DETERMINING REFERENCE SLOW WAVE ACTIVITY IN A SUBJECT

(71) Applicant: KONINKLIJKE PHILIPS N.V., Eindhoven (NL)

(72) Inventors: Gary Nelson Garcia Molina, Madison, WI (US); Anandi Mahadevan, Murrysville, PA (US); Surya Subrahmanya Sreeram Vissapragada Venkata Satya, Monroeville, PA (US); Annette Kapitan, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 245 days.

(21) Appl. No.: 16/466,357

(22) PCT Filed: Dec. 1, 2017

(86) PCT No.: PCT/EP2017/081142
§ 371 (c)(1),
(2) Date: Jun. 4, 2019

(87) PCT Pub. No.: WO2018/104163
PCT Pub. Date: Jun. 14, 2018

(65) Prior Publication Data
US 2020/0077919 A1 Mar. 12, 2020

Related U.S. Application Data

(60) Provisional application No. 62/430,407, filed on Dec. 6, 2016.

(51) Int. Cl.
*A61B 5/38* (2021.01)
*A61M 21/00* (2006.01)
*A61B 5/00* (2006.01)

(52) U.S. Cl.
CPC .............. *A61B 5/38* (2021.01); *A61B 5/4806* (2013.01); *A61M 21/00* (2013.01); *A61M 2021/0027* (2013.01)

(58) Field of Classification Search
CPC ........... A61M 21/00–02; A61B 5/4806–4815; A61B 5/38
See application file for complete search history.

(56) References Cited

U.S. PATENT DOCUMENTS

| 5,611,350 A | 3/1997 | John | |
|---|---|---|---|
| 2008/0081941 A1* | 4/2008 | Tononi | A61M 21/02 600/14 |

(Continued)

FOREIGN PATENT DOCUMENTS

| WO | WO-2015118415 A1 * | 8/2015 | ........... A61B 5/4815 |

OTHER PUBLICATIONS

Santaniello, S. et al., "Closed-Loop Control of Deep Brain Stimulation: A Simulation Study", IEEE Transactions on Neural Systems and Rehabilitation Engineering, IEEE Service Center, New York, NY, US, vol. 19, No. 1, Feb. 1, 2011.

(Continued)

*Primary Examiner* — Thaddeus B Cox

(57) ABSTRACT

The present disclosure pertains to a reference slow wave activity metric determination system. Instead of collecting information during sleep sessions without stimulation (e.g., baseline and/or sham sessions) to determine a reference amount of slow wave activity in a subject, the present system is configured to build a model between stimulation properties and slow wave enhancement, and determine the reference amount of slow wave activity in the subject (e.g., corresponding to what would occur during baseline sleep and/or sham sessions) using the model. Advantageously, this approach does not require performance of baseline and/or sham sleep sessions, and enables personalization of the (Continued)

reference amount of slow wave activity, which dynamically increases its accuracy as more information is collected.

12 Claims, 6 Drawing Sheets

(56) References Cited

U.S. PATENT DOCUMENTS

| | | |
|---|---|---|
| 2008/0194981 A1 | 8/2008 | Sarkela et al. |
| 2015/0038869 A1 | 2/2015 | Simon et al. |
| 2015/0148700 A1 | 5/2015 | Mhuircheartaigh et al. |
| 2016/0022168 A1* | 1/2016 | Luczak ............... A61N 1/0531 600/544 |
| 2016/0045706 A1 | 2/2016 | Garcia Molina et al. |
| 2016/0058970 A1 | 3/2016 | Garcia Molina et al. |
| 2016/0082222 A1 | 3/2016 | Garcia Molina et al. |
| 2016/0296164 A1 | 10/2016 | Garcia Molina |
| 2016/0302718 A1 | 10/2016 | Laura Lapoint et al. |
| 2018/0236232 A1* | 8/2018 | Soulet De Brugiere ............... A61B 5/38 |

OTHER PUBLICATIONS

Bellesi, M. et al., "Enhancement of sleep slow waves: underlying mechanisms and practical consequences", Frontiers in Systems Neuroscience, vol. 8, Oct. 28, 2014.

Hu, S. et al., "Identify the reference signal of scalp EEG recording", 2013 Sixth International Conference on Advanced Computational Intelligence, IEEE, Oct. 19, 2013.

Abo-Zahhad, M. et al., "State-of-the-art methods and future perspectives for personal recognition based on electroencephalogram signals", IET Biomet, IEEE, vol. 4, No. 3, Sep. 1, 2015.

Oikonomou et al., "A Kalman filter based methodology for EEG spike enhancement", Computer Methods and Programs in Biomedic, Elsevier, Amsterdam, NL, vol. 85, No. 2, Jan. 19, 2007.

Durrant Simon J et al: "Cross-modal transfer of statistical information benefits from sleep", Cortex, Elsevier Masson, Amsterdam, NL, vol. 78, Feb. 27, 2016.

Lopes Da Silva F et al: "Automatic detection and localization of epileptic foci", Electroencephalography and Clinical Neurophysiology, Elsevier, Amsterdam, NL, vol. 43, No. 1, Jul. 1, 1977.

Matthias Molle et al: "Hippocampal Sharp Wave-Ripples Linked to Slow Oscillations in Rat Slow-Wave Sleep", Journal of Neurophysiology, vol. 96, No. 1, Jul. 1, 2006.

Krishnaswamy Pavitra et al: "Reference-free harmonic regression technique to remove EEG-fMRI ballistocardiogram artifacts", Engineering in Medicine and Biology Society (EMBC), 2013 35th Annual International Conference of the IEEE, IEEE, Jul. 3, 2013.

International Search Report and Written Opinion, International Application No. PCT/EP2017/081142, dated Feb. 22, 2018.

H.-V. V Ngo, J. C. Claussen, J. Born, and M. Mölle, "Induction of slow oscillations by rhythmic acoustic stimulation.," J. Sleep Res., p. 10 pp, Aug. 2012.

H.-V. V Ngo, T. Martinetz, J. Born, and M. Molle, "Auditory Closed-Loop Stimulation of the Sleep Slow Oscillation Enhances Memory," Neuron, vol. 78, No. May, pp. 1-9, 2013.

G. Santostasi, R. Malkani, B. A. Riedner, M. Bellesi, G. Tononi, K. A. Paller, and P. C. Zee, "Phase-locked loop for precisely timed acoustic stimulation during sleep," J. Neurosci. Methods, pp. 1-14, 2015.

B. A. Riedner, B. K. Hulse, F. Ferrarelli, S. Sarasso, and G. Tononi, "Enhancing sleep slow waves with natural stimuli," Medicamundi, vol. 45, No. 2, pp. 82-88, 2010.

G. Tononi and C. Cirelli, "Sleep and the price of plasticity: from synaptic and cellular homeostasis to memory consolidation and integration.," Neuron, vol. 81, No. 1, pp. 12-34, Jan. 2014.

A. H. Sayed, "Recursive Least-Squares," in Adaptive Filters, John Wiley & Sons, 2008, pp. 492-500.

* cited by examiner

SYSTEM AND METHOD FOR DETERMINING REFERENCE SLOW WAVE ACTIVITY IN A SUBJECT

CROSS-REFERENCE TO PRIOR APPLICATIONS

This application is the U.S. National Phase application under 35 U.S.C. § 371 of International Application Serial No. PCT/EP2017/081142, filed on 1 Dec. 2017, which claims the benefit of U.S. Application Ser. No. 62/430,407, filed on 6 Dec. 2016. These applications are hereby incorporated by reference herein.

BACKGROUND

1. Field

The present disclosure pertains to a system and method for determining a reference slow wave activity (SWA) metric for a subject using information from sleep sessions with SWA enhancing stimulation provided to the subject.

2. Description of the Related Art

Systems for monitoring sleep are known. The restorative value of sleep can be increased by delivering appropriately timed auditory stimulation during deep sleep to enhance sleep slow waves. Typically, the restorative value of sleep is determined based on sham/baseline nights of sleep where no stimulation is provided to a subject. The present disclosure overcomes deficiencies in prior art systems.

SUMMARY

Accordingly, one or more aspects of the present disclosure relate to a reference slow wave activity metric determination system. The system comprises one or more stimulators, one or more sensors, one or more hardware processors, and/or other components. The one or more stimulators are configured to provide stimulation to a subject. The one or more sensors are configured to generate output signals conveying information related to slow wave activity in the subject and stimulation provided to the subject during sleep sessions. The one or more hardware processors operatively communicate with the one or more stimulators and the one or more sensors. The one or more hardware processors are configured by machine-readable instructions to: control the one or more stimulators to provide stimulation to the subject during the sleep sessions according to a predetermined therapy regime; determine a sleep session slow wave activity metric and a sleep session stimulation metric for a given sleep session based on the output signals; compare the sleep session slow wave activity metric to a reference slow wave activity metric determined based on prior sleep sessions where stimulation was provided to the subject; and determine an updated reference slow wave activity metric based on the comparison and the sleep session stimulation metric.

Yet another aspect of the present disclosure relates to a reference slow wave activity metric determination method. The method is performed with a determination system. The determination system comprises one or more stimulators, one or more sensors, one or more hardware processors, and/or other components. The method comprises: controlling, with the one or more hardware processors, the one or more stimulators to provide stimulation to a subject during sleep sessions according to a predetermined therapy regime; generating, with the one or more sensors, output signals conveying information related to slow wave activity in the subject and stimulation provided to the subject during sleep sessions; determining, with the one or more hardware processors, a sleep session slow wave activity metric and a sleep session stimulation metric for a given sleep session based on the output signals; comparing, with the one or more hardware processors, the sleep session slow wave activity metric to a reference slow wave activity metric determined based on prior sleep sessions where stimulation was provided to the subject; and determining, with the one or more hardware processors, an updated reference slow wave activity metric based on the comparison and the sleep session stimulation metric.

Still another aspect of present disclosure relates to a reference slow wave activity metric determination system. The system comprises: means for providing stimulation to a subject during sleep sessions; means for controlling the means for providing stimulation to provide stimulation to the subject during sleep sessions according to a predetermined therapy regime; means for generating output signals conveying information related to slow wave activity in the subject and stimulation provided to the subject during sleep sessions; means for determining a sleep session slow wave activity metric and a sleep session stimulation metric for a given sleep session based on the output signals; means for comparing the sleep session slow wave activity metric to a reference slow wave activity metric determined based on prior sleep sessions where stimulation was provided to the subject; and means for determining an updated reference slow wave activity metric based on the comparison and the sleep session stimulation metric.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
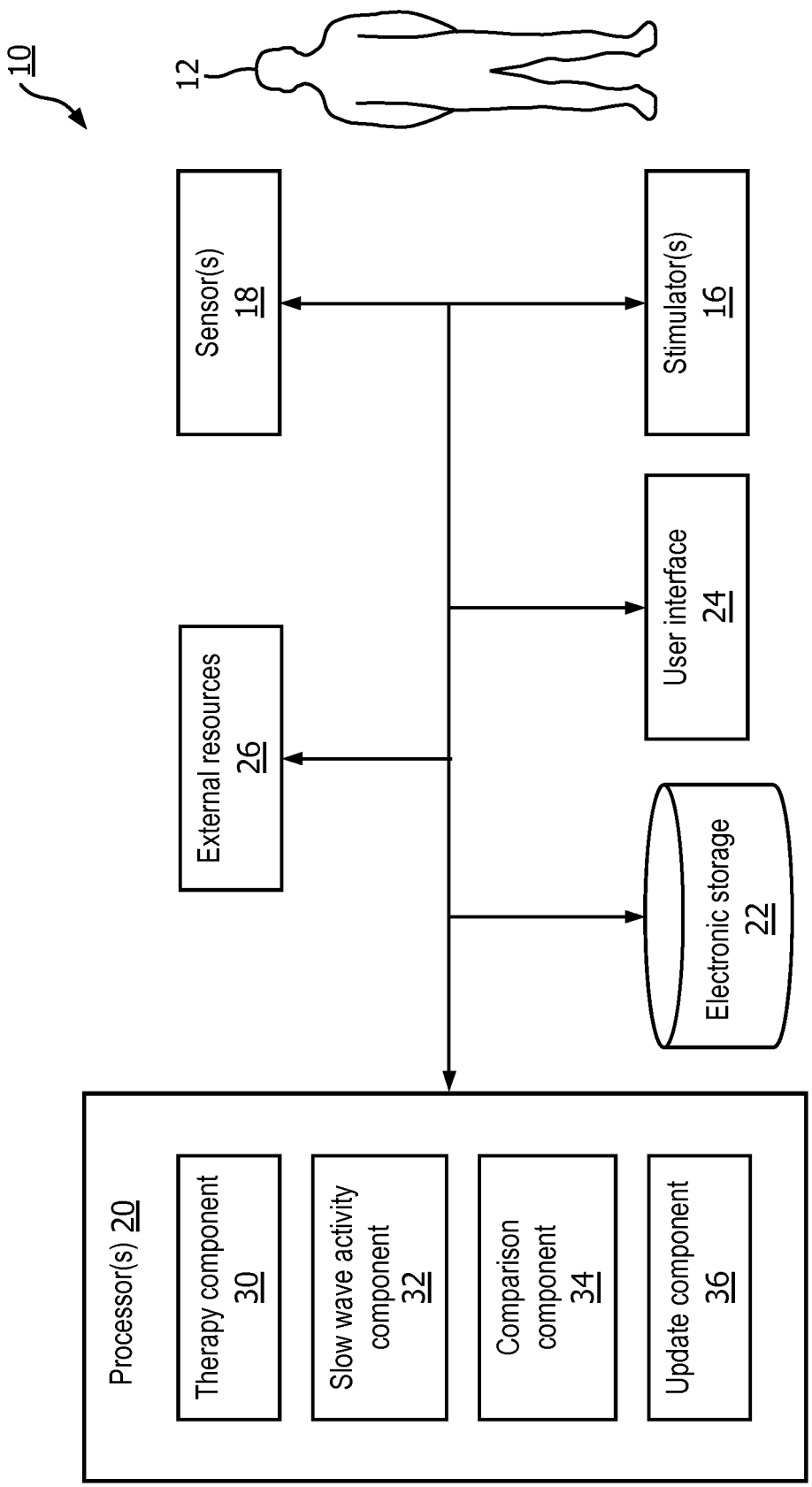
FIG. 1 illustrates a reference slow wave activity metric determination system.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a reference slow wave activity (SWA) metric determination system 10. Instead of collecting information during sleep sessions without stimulation (e.g., baseline and/or sham sessions) to determine a reference amount of SWA in a subject 12, system 10 is configured to build a model between stimulation properties and slow wave enhancement based on information generated during sleep sessions where stimulation is delivered to subject 12, and determine the reference amount of SWA in the subject (e.g., corresponding to what would occur during baseline sleep and/or sham sessions) using the model. Advantageously, this approach does not require performance of baseline and/or sham sleep sessions, and enables personalization of the reference amount of SWA, which dynamically increases its accuracy as more information is collected.

System 10 is configured such that subject 12 and/or other users receive feedback on the enhancement effect of stimulation after individual sleep sessions where system 10 is used. Typically, such feedback is given in terms of the increase in a metric related to SWA relative to a reference level of SWA (e.g., a level of SWA that occurred in one or more baseline sleep sessions, or sleep sessions where no stimulation was provided). Typically, the reference amount of SWA can be personalized based on sham and/or baseline sleep sessions by a given individual, or derived from demographically (e.g. age range and gender) matched data. Typically, personalizing a reference SWA metric requires a user to record sleep sessions with a system where no stimulation is provided. To cope with night to night variability, periodic baseline sessions would need to be scheduled and be proposed to the user who needs to be informed of when baseline sleep is required. However knowing that a particular sleep session will not have stimulation may influence the user and compromise the integrity of the data (e.g., in the sense that the sleep session may not accurately reflect typical baseline sleep). In addition, a user may simply refuse to participate in recording baseline sleep sessions.

Using demographically (e.g., age range and/or gender) matched data to set reference SWA metric values has the advantage of removing (or at least decreasing) the need to ask a user to perform baseline recordings. However, this approach requires a critical mass of data for the reference SWA metric values from across a similar population of users to be meaningful and statistically appropriate. In addition, reference SWA metric values determined in this way are less personalized to individual users.

System 10 overcomes limitations of prior art systems by determining a reference SWA metric for subject 12 based on sleep sessions where stimulation is provided to subject 12, without the need for sham/baseline sessions. In some embodiments, system 10 includes one or more of a sensory stimulator 16, a sensor 18, a processor 20, electronic storage 22, a user interface 24, external resources 26, and/or other components.

Sensory stimulator 16 is configured to provide electric, magnetic, and/or sensory stimulation to subject 12. Sensory stimulator 16 is configured to provide electric, magnetic, and/or sensory stimulation to subject 12 prior to a sleep session, during a sleep session, and/or at other times. For example, sensory stimulator 16 may be configured to provide stimuli to subject 12 during a sleep session to facilitate a transition to a deeper stage of sleep, a lighter stage of sleep, maintain sleep in a specific stage, and/or for other purposes. In some embodiments, sensory stimulator 16 may be configured such that facilitating a transition between deeper sleep stages and lighter sleep stages includes decreasing sleep slow waves in subject 12, and facilitating a transition between lighter sleep stages and deeper sleep stages includes increasing sleep slow waves.

Sensory stimulator 16 is configured to facilitate transitions between sleep stages and/or maintain sleep in a specific stage through non-invasive brain stimulation and/or other methods. Sensory stimulator 16 may be configured to facilitate transitions between sleep stages and/or maintain sleep in a specific stage through non-invasive brain stimulation using electric, magnetic, and/or sensory stimuli. The electric, magnetic, and/or sensory stimulation may include auditory stimulation, visual stimulation, somatosensory stimulation, electrical stimulation, magnetic stimulation, a combination of different types of stimulation, and/or other stimulation. The electric, magnetic, and/or sensory stimuli include odors, sounds, visual stimulation, touches, tastes, somato-sensory stimulation, haptic, electrical, magnetic, and/or other stimuli. For example, acoustic tones may be provided to subject 12 to facilitate transitions between sleep stages and/or maintain sleep in a specific stage. Examples of sensory stimulator 16 may include one or more of a sound generator, a speaker, a music player, a tone generator, one or more electrodes on the scalp of subject 12, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, sensory stimulator 16 is configured to adjust the intensity, timing, and/or other parameters of the stimulation provided to subject 12.

Sensor 18 is configured to generate output signals conveying information related to brain activity, activity of the central nervous system, activity of the peripheral nervous system, and/or other activity in subject 12. In some embodiments, sensor 18 is configured to generate output signals conveying information related to SWA in subject 12. In some embodiments, the information related to brain activity, activity of the central nervous system, activity of the peripheral nervous system, and/or other activity in subject 12 is the information related to SWA. In some embodiments, sensor 18 is configured to generate output signals conveying information related to stimulation provided to subject 12 during sleep sessions.

In some embodiments, the SWA of subject 12 may correspond to a sleep stage of subject 12. The sleep stage of subject 12 may be associated with rapid eye movement (REM) sleep, non-rapid eye movement (NREM) sleep, and/or other sleep. The sleep stage of subject 12 may be one or more of NREM stage N1, stage N2, stage N3, or stage N4 sleep, REM sleep, and/or other sleep stages. In some embodiments, NREM stage 3 and/or 4 may be slow wave (e.g., deep) sleep. Sensor 18 may comprise one or more sensors that measure such parameters directly. For example, sensor 18 may include electroencephalogram (EEG) electrodes configured to detect electrical activity along the scalp of subject 12 resulting from current flows within the brain of subject 12. Sensor 18 may comprise one or more sensors that generate output signals conveying information related to SWA of subject 12 indirectly. For example, one or more sensors 18 may comprise a heart rate sensor that generates an output based on a heart rate of subject 12 (e.g., sensor 18 may be a heart rate sensor than can be located on the chest of subject 12, and/or be configured as a bracelet on a wrist of subject 12, and/or be located on another limb of subject 12), movement of subject 12 (e.g., sensor 18 may comprise an accelerometer that can be carried on a wearable, such as a bracelet around the wrist and/or ankle of subject 12 such that sleep may be analyzed using actigraphy signals), respiration of subject 12, and/or other characteristics of subject 12.

In some embodiments, the one or more sensors comprise one or more of the EEG electrodes, an electrooculogram (EOG) electrode, an actigraphy sensor, an electrocardiogram (EKG) electrode, a respiration sensor, a pressure sensor, a vital signs camera, a photoplethysmogram (PPG) sensor, a functional near infra-red sensor (fNIR), a temperature sensor, a microphone and/or other sensors configured to generate output signals related to (e.g., the quantity, frequency, intensity, and/or other characteristics of) the stimulation provided to subject 12, and/or other sensors. Although sensor 18 is illustrated at a single location near subject 12, this is not intended to be limiting. Sensor 18 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), coupled with a bed and/or other furniture where subject 12 is sleeping, and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, user interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical user interfaces configured to facilitate user interaction with system 10.

As shown in FIG. 1, processor 20 is configured to execute one or more computer program components. The computer program components may comprise software programs and/or algorithms coded and/or otherwise embedded in processor 20, for example. The one or more computer program components may comprise one or more of a therapy component 30, a slow wave activity component 32, a comparison component 34, an update component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Therapy component 30 is configured to control one or more stimulators 16 to provide stimulation to subject 12 during sleep sessions. The one or more stimulators 16 are controlled to provide stimulation according to a predetermined therapy regime. Sleep slow waves can be enhanced through (e.g. peripheral auditory, magnetic, electrical, and/or other) stimulation delivered in NREM sleep. Enhancing sleep slow waves increases the restorative value of sleep. Therapy component 30 monitors the brain activity of subject 12 based on the output signals of sensors 18 (e.g., based on an EEG) and/or other information during sleep sessions and controls the delivery of stimulation (e.g., auditory and/or other stimulation) by stimulator 16 to control SWA in subject 12 without disturbing sleep. In some embodiments, therapy component 30 performs operations similar to and/or the same as the operations described in U.S. patent application Ser. No. 14/784,782 (entitled "System and Method for Sleep Session Management Based on Slow Wave Sleep Activity in a Subject"), Ser. No. 14/783,114 (entitled "System and Method for Enhancing Sleep Slow Wave Activity Based on Cardiac Activity"), Ser. No. 14/784,746 (entitled "Adjustment of Sensory Stimulation Intensity to Enhance Sleep Slow Wave Activity"), Ser. No. 15/101,008 (entitled "System and Method for Determining Sleep Stage Based on Sleep Cycle"), and/or Ser. No. 15/100,435 (entitled "System and Method for Facilitating Sleep Stage Transitions"), which are all individually incorporated by reference in their entireties.

Figure 2:
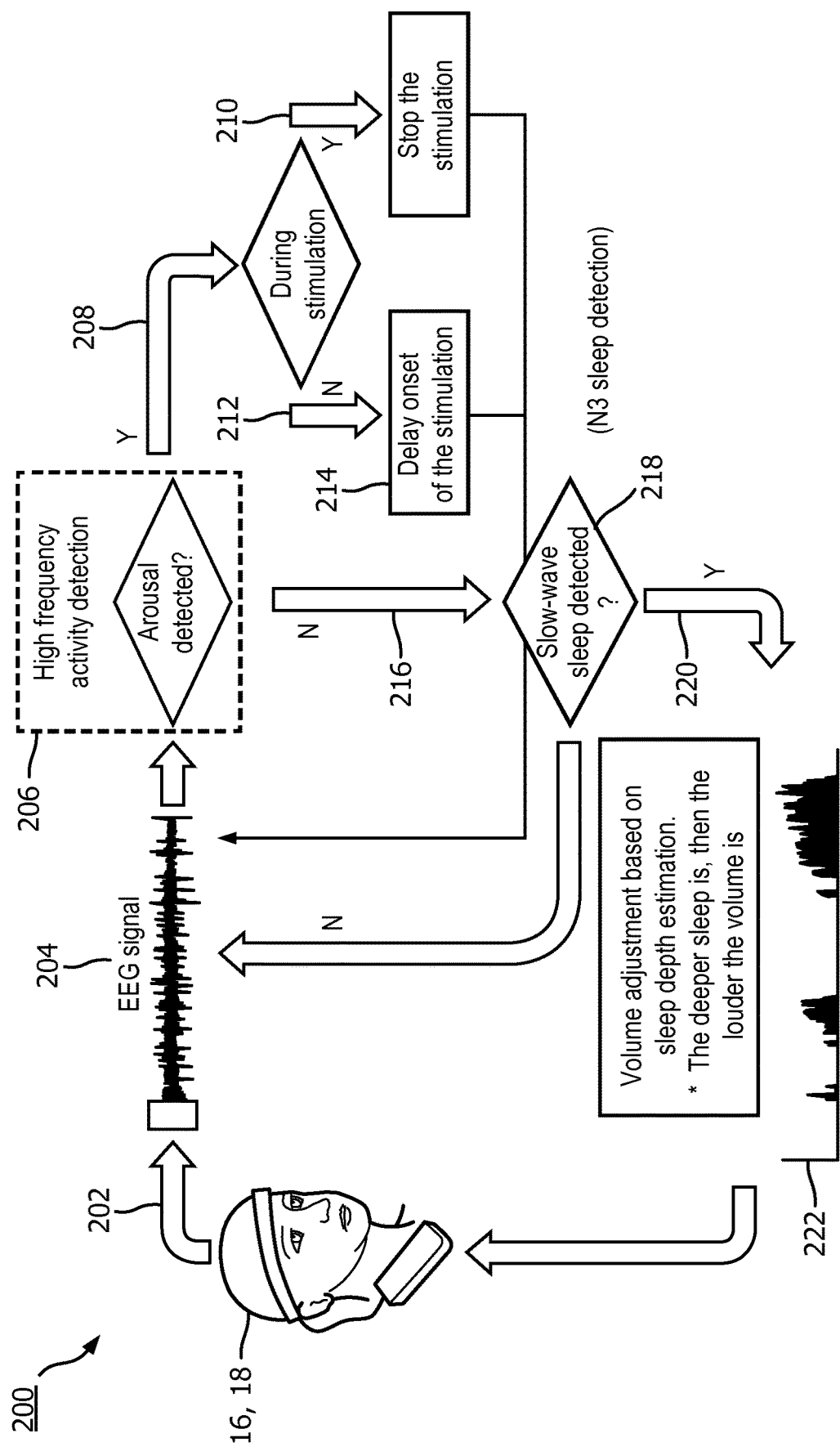
FIG. 2 illustrates an example of the operations performed by a therapy component of a processor of the system.

An example illustration of the operations 200 performed by therapy component 30 (shown in FIG. 1) is shown in FIG. 2. As shown in FIG. 2, EEG electrodes (e.g., sensors 18) generate 202 an EEG signal 204. The presence of EEG patterns (high power in the alpha 8-12 Hz and/or beta 15-30 Hz bands) indicative of (micro) arousals is evaluated 206 by therapy component 30 (FIG. 1). If arousal-like activity is detected 208 in the EEG during stimulation therapy component 30 controls stimulator 16 to stop 210 the stimulation.

If the arousal-like activity is detected 212 outside the stimulation period, the onset of the next stimulation is delayed 214. If no arousal-like activity is detected 216, then therapy component 30 attempts to detect 218 deep sleep based on the power in the SWA band (0.5 to 4 Hz), the temporal density of detected slow-waves, and/or other information. Responsive to detection of sufficiently deep sleep 220, therapy component 30 is configured to control stimulator 16 such that auditory (as in the example shown in FIG. 2 but this is not intended to be limiting) stimulation is delivered 222. Therapy component 30 is configured such that the volume (for example) of the auditory (for example) stimulation is modulated by a real time EEG based estimation of sleep depth that considers the sum of power ratios: delta power/alpha power+delta power/beta power. Consequently, the deeper sleep is, the louder the volume of the stimulation becomes.

Returning to FIG. 1, slow wave activity component 32 is configured to determine a sleep session SWA metric, a sleep session stimulation metric, and/or other information for a given sleep session. The sleep session SWA metric is a metric quantifying SWA in subject 12 for a given sleep session. The sleep session stimulation metric quantifies the stimulation provided to subject 12 during the given sleep session. The sleep session SWA metric and the sleep session stimulation metric are determined based on the output signals and/or other information. In some embodiments, the sleep session SWA metric comprises average power in a 0.5 to 4 Hz band of an EEG across NREM sleep for the given sleep session, total accumulated power for the given sleep session, total and/or cumulative SWA (CSWA) during detected (and/or annotated e.g., by a technician) NREM sleep during the sleep session, power in the slow oscillation band (e.g., about 0.5 to about 2 Hz), count of slow wave events, average amplitude of detected slow waves, and/or other metrics. CSWA and/or other sleep session SWA metrics, for example, are related to the total restorative value of sleep. In some embodiments, the sleep session stimulation metric comprises a number of tones played during the given sleep session, an average volume of tones played during the given sleep session, number of tones within a defined volume range (e.g. between about 45 to about 60 dB), number of tones delivered within a pre-defined time interval with respect to a detected slow-wave event (e.g., this can be used to count the number of tones in-phase or out of phase), number of tones per sleep cycle (e.g., a sleep cycle comprises NREM/REM complete sleep periods and lasts for approximately 90 minutes), and/or other metrics.

Comparison component 34 is configured to compare the sleep session SWA metric to a reference SWA metric. The reference SWA metric quantifies typical SWA in subject 12 during sleep sessions where no stimulation is provided to subject 12. However, the reference SWA metric is determined based on prior sleep sessions where stimulation was provided to the subject (e.g., as described below). In some embodiments, the reference SWA metric is determined based on a first determined slesp session SWA metric for a first sleep session. In some embodiments, the reference SWA metric is determined based on a combination of the first determined SWA metric with additional previously determined sleep session SWA metrics for previous sleep sessions of subject 12.

In some embodiments, the sleep session SWA metric is compared to the reference SWA metric to determine SWA enhancement in subject 12 for the given sleep session. In some embodiments, the comparison and/or the enhancement determination comprises determining a difference between the sleep session SWA metric and the reference SWA metric, and normalizing the difference by the reference SWA metric.

For example, the sleep session SWA metric of session "i" ($SWA_i$) is used to estimate the enhancement in the restorative quality of sleep (e.g., slow wave enhancement) facilitated by system 10 by comparing $SWA_i$ to the reference SWA metric ($\overline{SWA}$). As described above, the reference SWA metric ($\overline{SWA}$) is representative of a baseline sleep session where no stimulation was provided, but is actually determined based on information from sleep sessions where stimulation was provided. In some embodiments, comparison component 34 is configured to cause the information related to SWA enhancement to be displayed to subject 12 and/or other users via user interface 24, external resources 26, and/or other components of system 10. In this example, the sleep session stimulation metric $P_i$ for session "i" may be the number of tones played and/or other metrics.

Update component 36 is configured to determine an updated reference SWA metric and/or other information. The updated reference SWA metric is determined based on the comparison, the sleep session stimulation metric, and/or other information. Update component 36 is configured to sequentially update the reference SWA metric with information determined (e.g., the comparison, the sleep session stimulation metric, and/or other information) for individual additional sleep sessions of subject 12. For example, update component 36 is configured to update the reference SWA metric for subject 12 after each night of sleep of subject 12.

Update component 36 is configured such that the properties (e.g., number of tones played) of the stimulation ($P_i$) in session "i" and $SWA_i$ are used to refine the estimation of $\overline{SWA}$. In some embodiments, determining the updated reference SWA metric ($\overline{SWA}$) comprises plotting the SWA enhancement relative to the sleep session stimulation metric for the given sleep session with previous SWA enhancements and corresponding previous sleep session stimulation metrics for previous sleep sessions, fitting a curve to the plotting, and determining the updated reference SWA metric based on the curve fit. In some embodiments, the curve fit is linear and/or non-linear.

Update component 36 is configured to update the reference SWA metric ($\overline{SWA}$) based on the sleep session stimulation metric ($P_i$) and the slow wave activity metric $SWA_i$ in session "i" according to the model described in Equation 1 below. By way of a non-limiting example, the model relating the SWA enhancement and stimulation properties is linear (e.g., which may be generalized to non-linear embodiments using a first order approximation and/or other methods):

$$100 \frac{SWA_i - \overline{SWA}}{\overline{SWA}} = kP_i + \Delta, \quad (1)$$

where the left side in Equation 1 represents the SWA enhancement as a percentage, k is the slope of the linear model and $\Delta$ is the offset. After completing N sleep sessions, a set of results $\{(SWA_i, P_i) | i=1, \ldots, N\}$ (where i is the index of the session) is available. Using the model in Equation 1, the following (Equation 2 to Equation 4) holds:

$$100 SWA_i \frac{1}{\overline{SWA}} - P_i k - \Delta = 100; i = 1, \ldots, N, \quad (2)$$

-continued $$\Rightarrow \begin{bmatrix} 100SWA_1 & -P_1 & -1 \\ \vdots & \vdots & \vdots \\ 100SWA_N & -P_N & -1 \end{bmatrix} \begin{bmatrix} \frac{1}{\overline{SWA}} \\ k \\ \Delta \end{bmatrix} = \begin{bmatrix} 100 \\ \vdots \\ 100 \end{bmatrix}, \quad (3)$$

$$M\left[\frac{1}{\overline{SWA}}, k, \Delta\right]^T = 100\vec{1}_N, \quad (4)$$

where M is the matrix $$\begin{bmatrix} 100SWA_1 & -P_1 & -1 \\ \vdots & \vdots & \vdots \\ 100SWA_N & -P_N & -1 \end{bmatrix} \quad (5)$$

$(\bullet)^T$ is the matrix operator, and $\vec{1}_N$ is the N×1 column vector with elements equal to 1. The matrix notation in Equation 4, for example, facilitates sequential updating of the values of the model parameters (1/$\overline{SWA}$), k, and Δ as more information from additional sleep sessions becomes available.

As described above, update component 36 is configured to sequentially update (1/$\overline{SWA}$), k, and Δ. Update component 36 is configured such that information from the "i"-th sleep session are grouped into a vector noted as:

$$x_i = [100SWA_i, -P_i, -1]^T \quad (6)$$

and the corresponding values of model parameters are also grouped into a vector noted as:

$$w_i = \left[\frac{1}{\overline{SWA_i}}, k_i, \Delta_i\right]^T. \quad (7)$$

In some embodiments, comparison component 34 and/or update component 36 are configured such that, using a recursive least squares approach and/or other approaches:

$$w_i = w_{i-1} - \Gamma_i x_i (x_i^T w_{i-1} - 100), \quad (8)$$

where $\Gamma_i$ can also be sequentially estimated, $$\Gamma_i = \Gamma_{i-1} - \frac{\Gamma_{i-1} x_i x_i^T \Gamma_{i-1}}{1 + x_i^T \Gamma_{i-1} x_i}, \quad (9)$$

and $\Gamma_0 = I_{3\times 3}$ (identity matrix of size 3, e.g., the same dimension as $x_i$). Comparison component 34 and/or update component 36 are configured such that the matrix $\Gamma_i$ is the inverse covariance matrix of the data $\{x_i = [100SWA_i - P_i, -1]^T = 1, \ldots, N\}$. Comparison component 34 and/or update component 36 are configured such that the estimation $w_i$ is then used to determine the enhancement metric for the next sleep (i+1) session. Initial conditions ($\overline{SWA_0}$, $k_0$, $\Delta_0$) are set to provide SWA enhancement estimations. In some embodiments, update component 36 is configured to facilitate user (e.g., subject 12 and/or other users such as doctors, nurses, family members, care givers, researchers, etc.) entry and/or selection of the initial conditions via user interface 24 and/or other components of system 10. In some embodiments, the initial conditions entered and/or selected by the user may be determined based on expertise of the user, based on information from baseline (e.g., where no stimulation was provided) sleep sessions of subject 12 and/or other subjects, based on information from sleep sessions of demographically similar subjects (e.g., demographically matched averages), and/or based on other information. Example set points are described in Table I below.

As described above, in some embodiments, slow wave activity component 32 is configured such that the sleep session stimulation metric is the total number of tones played. Slow wave activity component 32 is configured such that the sleep session stimulation metric is the total number of tones played because the number of tones delivered during a sleep session are statistically significant (e.g., p<1e-3 based on experimental results obtained using system 10) indicators of CSWA (e.g., the sleep session SWA metric) enhancement, and/or have the highest correlation (e.g., about 0.65 based on experimental results obtained using system 10) predictor of the enhancement of CSWA in stimulation sleep sessions as compared to sham sessions (e.g., sessions where no stimulation is delivered to subject 12).

Figure 3:
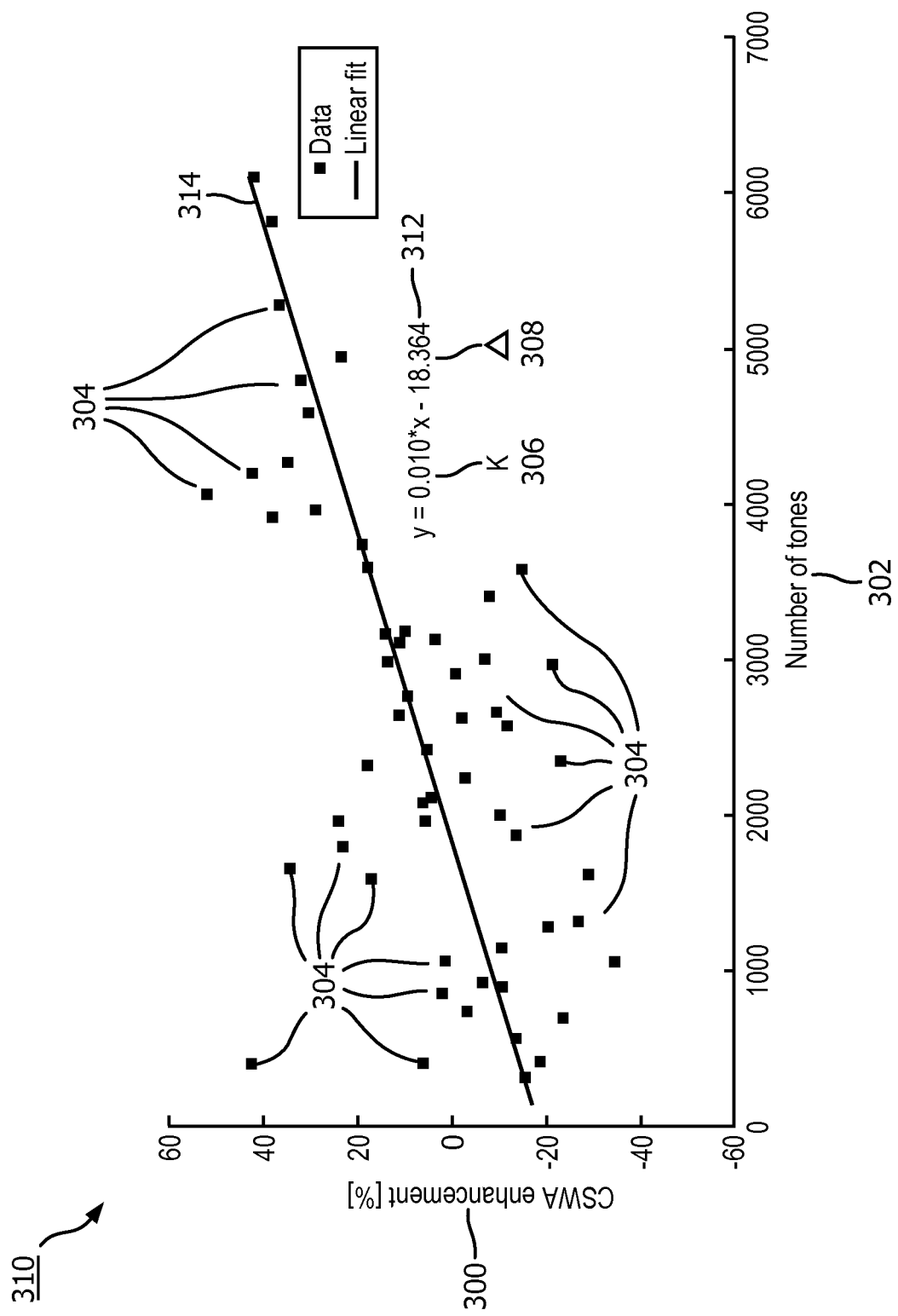
FIG. 3 illustrates cumulative slow wave activity (e.g., the sleep session SWA metric) enhancement for a given number of tones played (e.g., the sleep session stimulation metric) during individual sleep sessions.

FIG. 3 illustrates CSWA (e.g., the sleep session SWA metric) enhancement 300 for a given number of tones played 302 (e.g., the sleep session stimulation metric) during for individual sleep sessions 304. According to the model in Equation 1 described above, the values of k 306 and Δ 308 in this example are respectively 0.01 and −18. This example indicates that 100 tones lead to about a 1% enhancement in CSWA. The offset is related to the variability of baseline CSWA. The variability in this example can be expected to diminish as information from additional sleep sessions are included in the dataset (e.g., through the application of the sequential updating in Equation 8 and Equation 9 by update component 36 shown in FIG. 1). In FIG. 3, as information for individual sleep sessions 304 is added to plot 310 (e.g., by update component 36 shown in FIG. 1), the equation 312 (and hence k 306 and Δ 308) of the line 314 fit to the sleep session 304 information is updated. For the example shown in FIG. 3 the initial conditions were set as described in Table I (these values are only examples and are not intended to be limiting).

TABLE I

| Parameter | Initial value | Comment |
| --- | --- | --- |
| $\overline{SWA_0}$ | 1.7e+6 μV$^2$ | Corresponds to the average of baseline nights of 18 subjects. Alternatively this may be determined based on demographically matched averages. |
| $k_0$ | 0.01 | Corresponds to the overall estimation that 100 tones improves CSWA by ~1% |
| $\Delta_0$ | 10 | This assumes the variability of CSWA over baseline nights is 10%. |

It should be noted that system 10, at least by virtue of the sequentially updating algorithm described above, is configured to personalize these values to subject 12 over time as information from more and more sleep sessions of subject 12 is included in the determination of the updated reference SWA metric by update component 36 (FIG. 1).

Figure 4A:
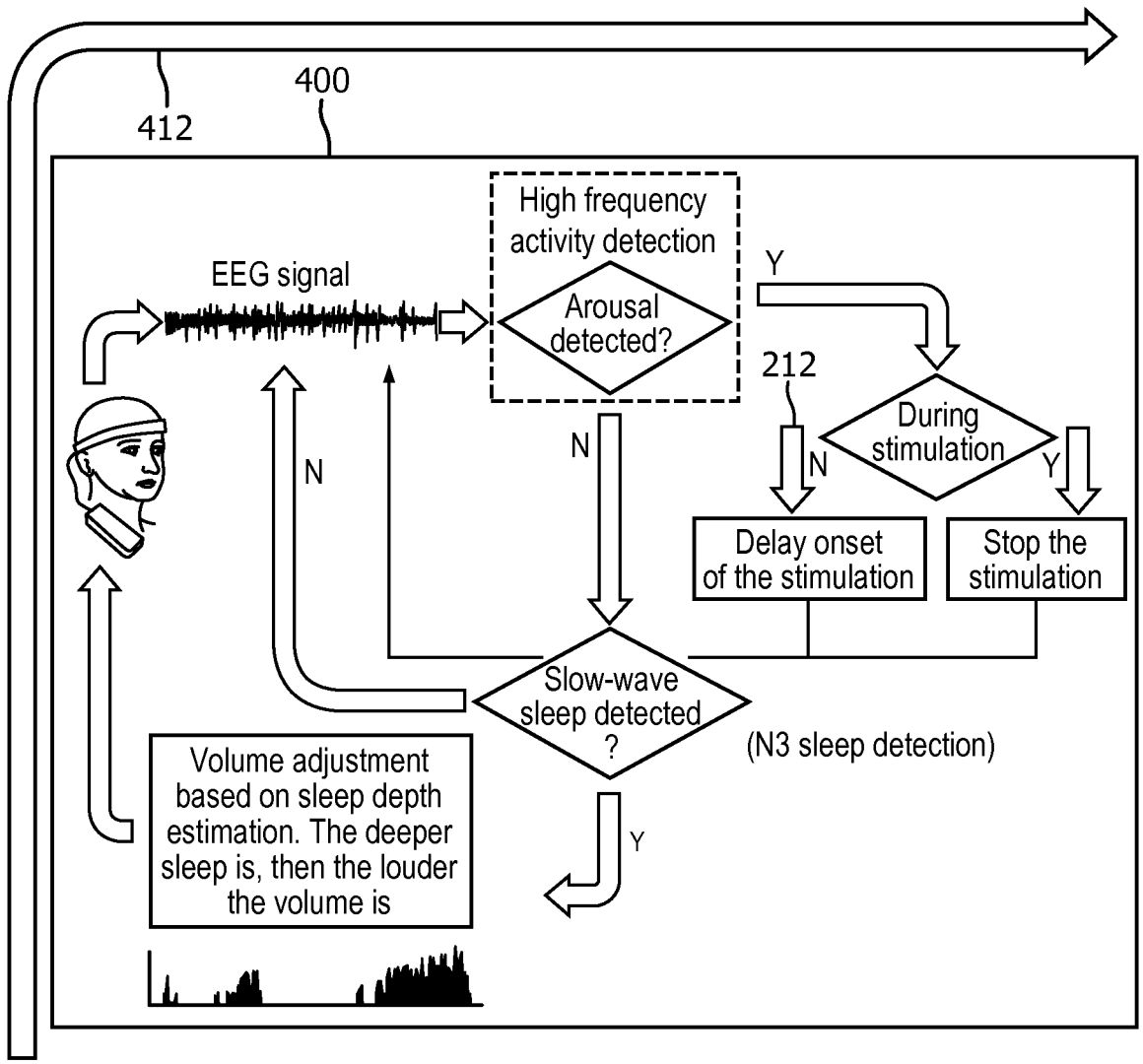
FIG. 4 illustrates a summary of the operations performed by the system.
Figure 4A:
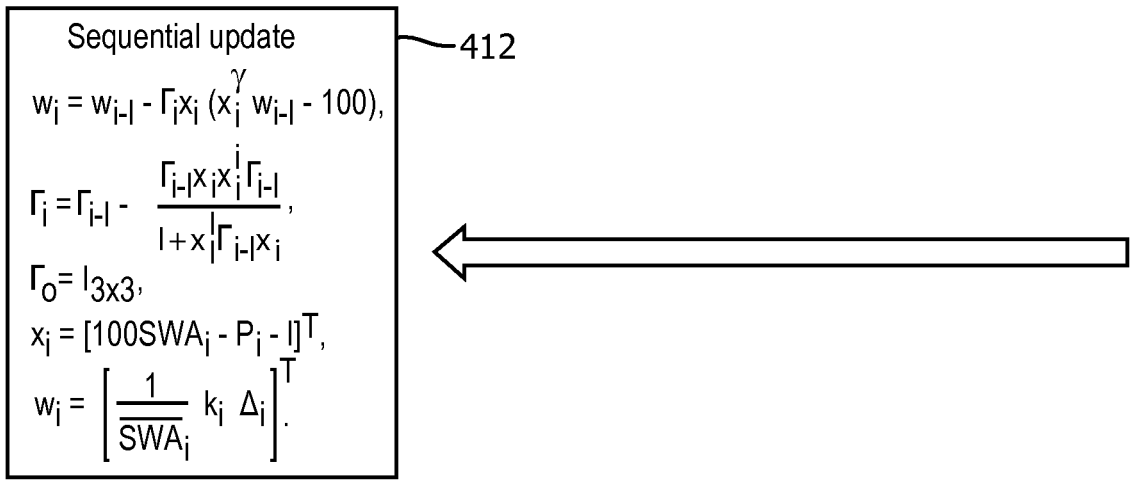
Figure 4B:
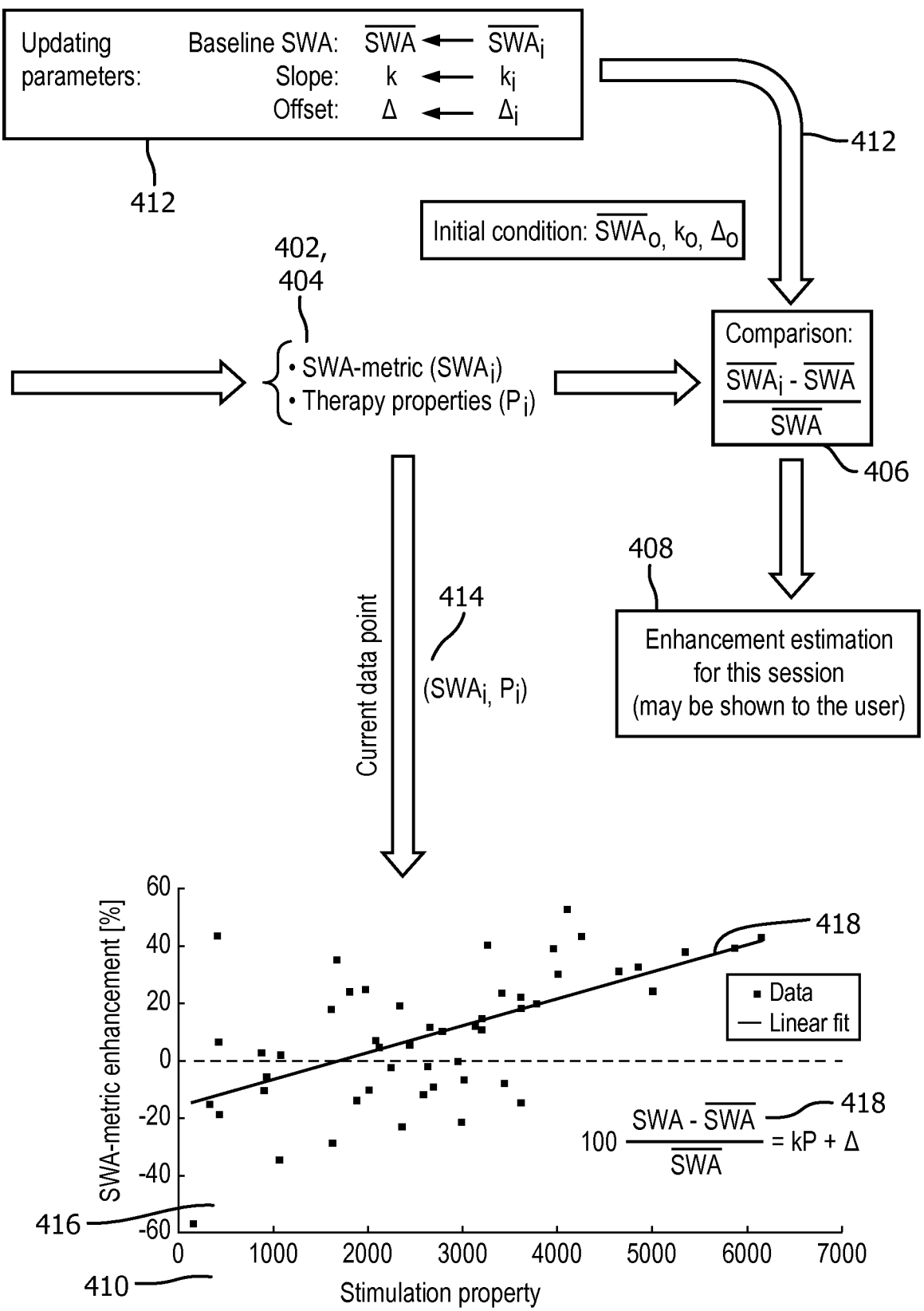

A summary of the operations of system 10 (FIG. 1) described above are illustrated in FIG. 4. As shown in FIG. 4, system 10 (e.g., therapy component 30 shown in FIG. 1) is configured to control 400 one or more stimulators to provide stimulation to subject during sleep sessions. The one or more stimulators are controlled 400 to provide stimulation according to a predetermined therapy regime. System 10 (e.g., slow wave activity component 32 shown in FIG. 1) is configured to determine 402, 404 a sleep session SWA metric (SWA$_i$), a sleep session stimulation metric (P$_i$), and/or other information for a given sleep session. System 10 (e.g., comparison component 34 shown in FIG. 1) is configured to compare 406 the sleep session SWA metric (SWA$_i$) to a reference SWA metric ($\overline{SWA}$). In some embodiments, the comparison comprises determining SWA enhancement 408 in the subject for a given sleep session relative to the SWA activity in the subject during sham/baseline sleep sessions. In some embodiments, comparison 406 and/or the enhancement determination 408 comprises determining a difference between the sleep session SWA metric and the reference SWA metric, and normalizing (e.g., as shown at comparison 406 in FIG. 4) the difference by the reference SWA metric. In FIG. 4, for example, the SWA metric of session "i" (SWA$_i$) is used to estimate the enhancement in the restorative quality of sleep (e.g., slow wave enhancement) facilitated by system 10 (FIG. 1) by comparing SWA$_i$ to the reference SWA metric ($\overline{SWA}$).

System 10 (e.g., update component 36 shown in FIG. 1) is configured to determine 410 an updated reference SWA metric and/or other information. The updated SWA metric is determined based on the comparison, the sleep session stimulation metric, and/or other information. System 10 (update component 36) is configured to sequentially update 412 the reference SWA metric with information determined 414 (e.g., the comparison, the sleep session stimulation metric, and/or other information) for individual additional sleep sessions of subject 12. For example, system 10 (update component 36) is configured to update the reference SWA metric for the subject after each night of sleep.

As shown in FIG. 4, system 10 (update component 36) is configured such that the properties (e.g., number of tones played) of the stimulation (P$_i$) in session "i" and SWA$_i$ are used to update the determination of $\overline{SWA}$. In some embodiments, determining the updated reference SWA metric ($\overline{SWA}$) comprises plotting 416 the SWA enhancement relative to the sleep session stimulation metric (e.g., 414) for the given sleep session with previous SWA enhancements and corresponding previous sleep session stimulation metrics for previous sleep sessions, fitting a curve 418 to the plotting, and determining the updated reference SWA metric based on the curve fit (e.g., based on k, Δ, and Equations 1-9 above).

Returning to FIG. 1, in some embodiments, therapy component 30, slow wave activity component 32, comparison component 34, update component 36, and/or other components are configured to determine the sleep session SWA metric, compare the sleep session SWA metric to the reference SWA metric, and determine the updated reference SWA metric based on the information from previous sleep sessions of subject 12 and/or based on information generated during actual sham/baseline sleep sessions for subject 12. For example, therapy component 30 may control system 10 to facilitate one or more sham/baseline sleep sessions for subject 12. Generally, in such embodiments, slow wave activity component 32, comparison component 34, update component 36, and/or other components are configured to attribute a higher importance and/or weighting to the information from the sham/baseline sleep sessions compared to information from sleep sessions with stimulation. The algorithm described above (e.g., Equation 8 and Equation 9 followed by update component 36) is configured to accommodate this change.

For example, let $x_i$ be the information from an actual sham/baseline sleep session, the weight for the baseline information can be increased by setting $x_{i+1} = x_i$ and updating accordingly.

$$w_i = w_{i-1} - \Gamma_i x_i (x_i^T w_{i-1} - 100), \quad (10)$$

$$w_{i+1} = w_i - \Gamma_i x_i (x_i^T w_i - 100), \quad (11)$$

Combining Equations 10 and 11 yields:

$$w_i = w_{i-1} - 2\Gamma_i x_i (x_i^T w_{i-1} - 100) + \Gamma_i x_i x_i^T \Gamma_i x_i (1 + x_i^T w_{i-1}). \quad (12)$$

In Equation 12, the increased weight associated with the sham/baseline sleep session is made explicit by the coefficient (e.g., "2") in the second term on the right side of the equation. The third term may be simplified by considering that $\Gamma_i$ is the inverse of the covariance matrix of $\{x_i\}$ which, in turn, may be approximated by $x_i x_i^T$. Therefore, $\Gamma x_i x_i^T = I$. With this simplification, Equation 12 becomes:

$$w_i \approx 2w_{i-1} - 2\Gamma_i x_i (x_i^T w_{i-1} - 100). \quad (13)$$

Electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG may be displayed to a caregiver via user interface 24. As another example, user interface 24 may be and/or be included in a computing device such as a desktop computer, a laptop computer, a smartphone, a tablet computer, and/or other computing devices. Such computing devices may run one or more electronic applications having graphical user interfaces configured to provide information to and/or receive information from users.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20 and/or other components of system 10. In some embodiments, user interface 24 is configured to communicate wirelessly with processor 20 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

External resources 26 includes sources of information (e.g., databases, websites, etc.), external entities participating with system 10 (e.g., a medical records system of a health care provider), medical and/or other equipment (e.g., lamps and/or other lighting devices, sound systems, audio and/or visual recording devices, etc.) configured to communicate with and/or be controlled by system 10, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. In some implementations, some or all of the functionality attributed herein to external resources 26 may be provided by resources included in system 10. External resources 26 may be configured to communicate with processor 20, user interface 24, sensor 18, electronic storage 22, sensory stimulator 16, and/or other components of system 10 via wired and/or wireless connections, via a network (e.g., a local area network and/or the internet), via cellular technology, via Wi-Fi technology, and/or via other resources.

In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, these components may be integrated in to a headset and/or other garments worn by subject 12 during sleep.

Figure 5:
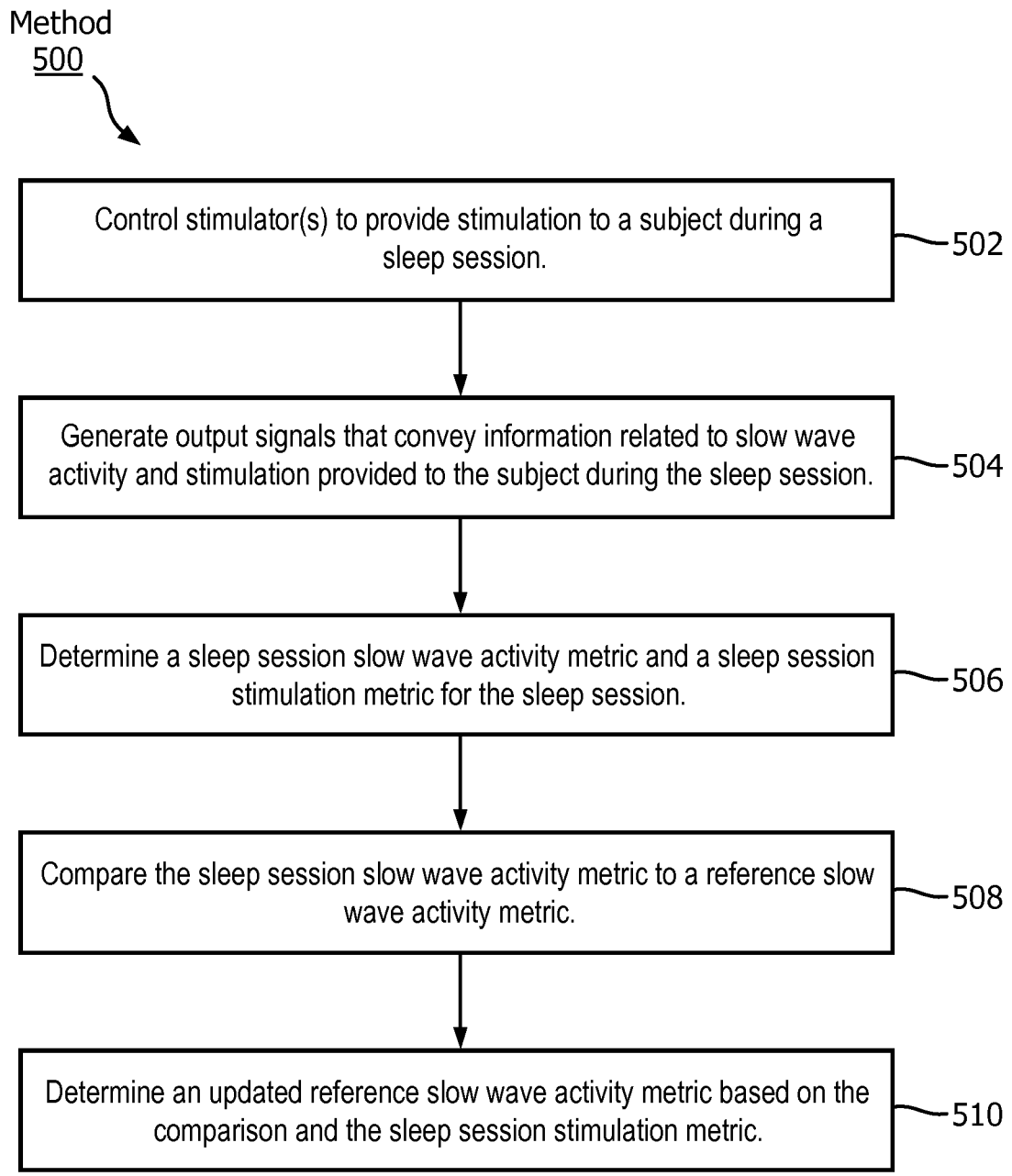
FIG. 5 illustrates a reference slow wave activity metric determination method.

FIG. 5 illustrates a reference SWA metric determination method 500 performed with a determination system. The determination system comprises one or more stimulators, one or more sensors, one or more hardware processors, and/or other components. The one or more hardware processors are configured to execute computer program components. The computer program components comprise a therapy component, a slow wave activity component, a comparison component, an update component, and/or other components. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, the one or more stimulators are controlled to provide stimulation to a subject during sleep sessions. In some embodiments, the one or more stimulators comprise a tone generator and/or other stimulators. The one or more stimulators are controlled to provide stimulation according to a predetermined therapy regime. In some embodiments, operation 502 is performed by a processor component the same as or similar to therapy component 30 (shown in FIG. 1 and described herein).

At an operation 504, output signals conveying information related to SWA in the subject and stimulation provided to the subject during the sleep sessions are generated. In some embodiments, the one or more sensors comprise electroencephalogram (EEG) sensors and/or other sensors configured to generate output signals conveying information related to SWA in the subject. In some embodiments, the one or more sensors comprise microphones (for example) and/or other sensors configured to generate output signals conveying information related to the stimulation provided to the subject. In some embodiments, operation 504 is performed by one or more sensors the same as or similar to sensors 18 (shown in FIG. 1 and described herein).

At an operation 506, a sleep session SWA metric and a sleep session stimulation metric are determined for a given sleep session. The SWA metric and the sleep session stimulation metric are determined based on the output signals and/or other information. In some embodiments, the sleep session SWA metric comprises one or more of average power in a 0.5 to 4 Hz band of an EEG for the given sleep session, or total accumulated power for the given sleep session. In some embodiments, the sleep session stimulation metric comprises one or more of a number of tones played during the given sleep session, or an average volume of tones played during the given sleep session. In some embodiments, operation 506 is performed by a processor component the same as or similar to slow wave activity component 32 (shown in FIG. 1 and described herein).

At an operation 508, the sleep session SWA metric is compared to a reference SWA metric. The reference SWA metric is determined based on prior sleep sessions where stimulation was provided to the subject. In some embodiments, the sleep session SWA metric is compared to the reference SWA metric to determine SWA enhancement in the subject for the given sleep session. In some embodiments, the comparison comprises determining a difference between the sleep session SWA metric and the reference SWA metric, and normalizing the difference by the reference slow wave activity metric. In some embodiments, operation 508 is performed by a processor component the same as or similar to comparison component 34 (shown in FIG. 1 and described herein).

At an operation 510, an updated reference SWA metric is determined. The updated SWA metric is determined based on the comparison, the sleep session stimulation metric, and/or other information. In some embodiments, determining the updated reference SWA metric comprises plotting the SWA enhancement relative to the sleep session stimulation metric for the given sleep session with previous SWA enhancements and corresponding previous sleep session stimulation metrics for previous sleep sessions, fitting a curve to the plotting, and determining the updated reference SWA metric based on the curve fit. In some embodiments, the curve fit is linear and/or non-linear. In some embodiments, operation 510 is performed by a processor component the same as or similar to update component 36 (shown in FIG. 1 and described herein).

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination

What is claimed is:

1. A reference sleep slow wave activity metric determination system comprising:
   one or more stimulators configured to provide stimulation to a subject;
   one or more sensors configured to generate output signals conveying information related to sleep slow wave activity in the subject and stimulation provided to the subject during sleep sessions; and
   one or more hardware processors operatively communicating with the one or more stimulators and the one or more sensors, the one or more hardware processors configured by machine-readable instructions to:
   control the one or more stimulators to provide stimulation to the subject during the sleep sessions according to a predetermined therapy regime;
   determine a sleep session sleep slow wave activity metric and a sleep session stimulation metric for a given sleep session based on the output signals;
   compare the sleep session sleep slow wave activity metric to a reference slow wave activity metric determined based on prior sleep sessions where stimulation was provided to the subject; and
   determine an updated reference sleep slow wave activity metric based on the comparison and the sleep session stimulation metric;
   wherein the one or more hardware processors are configured such that the sleep session sleep slow wave activity metric is compared to the reference sleep slow wave activity metric to determine sleep slow wave activity enhancement in the subject for the given sleep session, and such that the comparison comprises determining a difference between the sleep session sleep slow wave activity metric and the reference sleep slow wave activity metric and normalizing the difference by the reference sleep slow wave activity metric.

2. The system of claim 1, wherein the one or more sensors comprise electroencephalogram (EEG) sensors, the one or more stimulators comprise a tone generator, and the one or more hardware processors are configured such that:
   the sleep session sleep slow wave activity metric comprises one or more of average power in a 0.5 to 4 Hz band of an EEG for the given sleep session, or total accumulated power for the given sleep session; and
   the sleep session stimulation metric comprises one or more of a number of tones played during the given sleep session, an average volume of tones played during the given sleep session, or a number of tones per sleep cycle.

3. The system of claim 1, wherein the one or more hardware processors are configured such that determining the updated reference sleep slow wave activity metric comprises plotting the sleep slow wave activity enhancement relative to the sleep session stimulation metric for the given sleep session with previous sleep slow wave activity enhancements and corresponding previous sleep session stimulation metrics for previous sleep sessions, fitting a curve to the plotting, and determining the updated reference sleep slow wave activity metric based on the curve fit.

4. The system of claim 3, wherein the one or more hardware processors are configured such that the curve fit is linear or non-linear.

5. A reference sleep slow wave activity metric determination method, the method performed with a determination system, the determination system comprising one or more stimulators, one or more sensors, and one or more hardware processors, the method comprising:
   controlling, with the one or more hardware processors, the one or more stimulators to provide stimulation to a subject □ during sleep sessions according to a predetermined therapy regime;
   generating, with the one or more sensors, output signals conveying information related to sleep slow wave activity in the subject and stimulation provided to the subject during sleep sessions;
   determining, with the one or more hardware processors, a sleep session sleep slow wave activity metric and a sleep session stimulation metric for a given sleep session based on the output signals;
   comparing, with the one or more hardware processors, the sleep session sleep slow wave activity metric to a reference sleep slow wave activity metric determined based on prior sleep sessions where stimulation was provided to the subject; and
   determining, with the one or more hardware processors, an updated reference sleep slow wave activity metric based on the comparison and the sleep session stimulation metric;
   wherein the sleep session sleep slow wave activity metric is compared to the reference sleep slow wave activity metric to determine sleep slow wave activity enhancement in the subject for the given sleep session and wherein the comparison comprises determining a difference between the sleep session sleep slow wave activity metric and the reference sleep slow wave activity metric and normalizing the difference by the reference sleep slow wave activity metric.

6. The method of claim 5, wherein:
the one or more sensors comprise electroencephalogram (EEG) sensors;
the one or more stimulators comprise a tone generator;
the sleep session sleep slow wave activity metric comprises one or more of average power in a 0.5 to 4 Hz band of an EEG for the given sleep session, or total accumulated power for the given sleep session; and
the sleep session stimulation metric comprises one or more of a number of tones played during the given sleep session, an average volume of tones played during the given sleep session, or a number of tones per sleep cycle.

7. The method of claim 5, wherein determining the updated reference sleep low wave activity metric comprises plotting the sleep slow wave activity enhancement relative to the sleep session stimulation metric for the given sleep session with previous sleep slow wave activity enhancements and corresponding previous sleep session stimulation metrics for previous sleep sessions, fitting a curve to the plotting, and determining the updated reference sleep slow wave activity metric based on the curve fit.

8. The method of claim 7, wherein the curve fit is linear or non-linear.

9. A reference sleep slow wave activity metric determination system, the system comprising:
means for providing stimulation to a subject ☐ during sleep sessions;
means for controlling the means for providing stimulation to provide stimulation to the subject during sleep sessions according to a predetermined therapy regime;
means for generating output signals conveying information related to sleep slow wave activity in the subject and stimulation provided to the subject during sleep sessions;
means for determining a sleep session sleep slow wave activity metric and a sleep session stimulation metric for a given sleep session based on the output signals;
means for comparing the sleep session sleep slow wave activity metric to a reference sleep slow wave activity metric determined based on prior sleep sessions where stimulation was provided to the subject; and
means for determining an updated reference sleep slow wave activity metric based on the comparison and the sleep session stimulation metric;
wherein the sleep session sleep slow wave activity metric is compared to the reference sleep slow wave activity metric to determine sleep slow wave activity enhancement in the subject for the given sleep session and wherein the comparison comprises determining a difference between the sleep session sleep slow wave activity metric and the reference sleep slow wave activity metric and normalizing the difference by the reference sleep slow wave activity metric.

10. The system of claim 9, wherein:
the one or more sensors means for generating output signals comprise electroencephalogram (EEG) sensors;
the means for providing stimulation one or more stimulators comprise a tone generator;
the sleep session sleep slow wave activity metric comprises one or more of average power in a 0.5 to 4 Hz band of an EEG for the given sleep session, or total accumulated power for the given sleep session; and
the sleep session stimulation metric comprises one or more of a number of tones played during the given sleep session, an average volume of tones played during the given sleep session, or a number of tones per sleep cycle.

11. The system of claim 9, wherein determining the updated reference sleep slow wave activity metric comprises plotting the sleep slow wave activity enhancement relative to the sleep session stimulation metric for the given sleep session with previous sleep slow wave activity enhancements and corresponding previous sleep session stimulation metrics for previous sleep sessions, fitting a curve to the plotting, and determining the updated reference sleep slow wave activity metric based on the curve fit.

12. The method of claim 11, wherein the curve fit is linear or non-linear.

\* \* \* \* \*